United States Patent [19]

Wendler

[11] Patent Number: 5,211,640
[45] Date of Patent: May 18, 1993

[54] MALE URINARY INCONTINENCE DEVICE

[75] Inventor: Henrik G. Wendler, Frederiksberg, Denmark

[73] Assignee: Coloplast A/S, Denmark

[21] Appl. No.: 823,984

[22] Filed: Jan. 22, 1992

[30] Foreign Application Priority Data

Jan. 30, 1991 [DK] Denmark ............... 162/91

[51] Int. Cl.$^5$ ................................. A61F 5/44
[52] U.S. Cl. .................................. 604/349
[58] Field of Search .............. 604/349, 353; 206/69; 128/844, 842

[56] References Cited

U.S. PATENT DOCUMENTS

| 4,589,874 | 5/1986 | Riedel et al. | 604/349 |
| 4,626,250 | 12/1986 | Schneider | 604/349 |
| 4,656,675 | 4/1987 | Fajnsztajn | 604/349 |
| 4,769,099 | 9/1988 | Therriault et al. | 604/352 |
| 4,784,655 | 11/1988 | Campion et al. | 604/349 |

Primary Examiner—Randall L. Green
Assistant Examiner—Gina M. Gualtieri
Attorney, Agent, or Firm—Ostrolenk, Faber, Gerb & Soffen

[57] ABSTRACT

A male urinary incontinence device comprises an external catheter (1, 8), which at its distal end has a narrowed drainage tube (4) and in its supply condition is folded or rolled up on part of its length so that a portion of its inside faces outwards. An annular member (1, 10) separate from the catheter (1, 8) for use in applying the catheter is provided with an interior double-faced adhesive layer (7, 12) which is transferred to the inside of the catheter.

13 Claims, 2 Drawing Sheets

MALE URINARY INCONTINENCE DEVICE

BACKGROUND OF THE INVENTION

1. Field of the Invention

The invention relates to a male urinary incontinence device, comprising an external catheter for arrangement on the penis, having at its distal end a narrowed drainage tube for connection to a hose leading to a collection bag, which catheter in its supply condition is folded or rolled up on part of its length from the open proximal end, so that part of its inside is turned outwards, whereas in its applied condition the catheter surrounds the penis in its full length and is fastened hereto by means of an interior adhesive layer.

2. Description of the Related Art

Urinary incontinence devices with external catheters or urisheaths are well known for remedying male incontinence problems. Whereas the adhesive necessary to fasten the catheter on the penis conventionally has comprised a separate adhesive tape which was wound around the penis prior to applying the catheter, e.g. EP patent No. 0390 720 and U.S. Pat. No. 4,475,910 disclose catheter embodiments with an integrated adhesive which in the rolled-up supply condition of the catheter is positioned between the windings of the rolled-up part of the catheter as, furthermore, a layer of an adhesive release agent is provided between the adhesive and the exterior of the catheter in order to ensure that the adhesive remains on or is transferred to the interior of the catheter during application.

With these more modern catheter embodiments a greater comfort is obtained for the user, but production is complicated due to the application of the layers of adhesive and release agent which must be done in separate stages of the process.

For catheters made of latex it is furthermore necessary to use adhesives which with a view to the rolling-out function can be applied in a very thin layer so as to avoid cold creep of the adhesives and the catheter at long-term storage in the rolled-up condition of the catheter and which also do not have a disintegrating effect on the latex at long-term storage. This has made it difficult or impossible to use a number of adhesives that are very gentle to the skin.

SUMMARY OF THE INVENTION

As opposed to the above known prior art, the urinary incontinence device according to the invention is characterized in that an annular member separate from the catheter and intended for use in application of the catheter is provided with an adhesive layer on the inside, so that when the distal end of the catheter has been placed on the penis glans and the annular member is passed thereover, the adhesive layer is transferred to said part of the inside of the catheter, providing the interior adhesive layer.

According to the invention the requirement for using a separate adhesive tape prior to application of the catheter is avoided. The catheter proper can be manufactured by known production methods with an increased freedom in respect of choice of material. Since the adhesive does not enter into contact with the catheter during long-term storage an increased freedom is likewise obtained as regards the choice of adhesive. The adhesive layer on the ring-shaped member may consist of a thin double-faced adhesive tape or an adhesive applied in liquid form.

In an embodiment where in the supply condition the catheter is rolled-up on said part of its length the ring-shaped member may be made as a ring of a relatively inexpensive disposable material, e.g. cardboard, and with a diameter that does not exceed the diameter of the bead formed by the rolled-up portion of the catheter but is larger than the shaft diameter of the applied catheter. The adhesive layer may in its supply condition be covered by a tear-off cover foil known per se.

By designing said ring with an axial length larger than that of the adhesive layer placed on its inside the possibility of adjusting the arrangement of the adhesive layer on the inside of the catheter is obtained, since part of the rolled-up portion can be rolled out before the transfer begins by means of a part of the ring placed in front of the adhesive layer in the direction of application when the adhesive layer gets into contact with the rolled-up portion. A part of the ring placed behind the adhesive layer in the direction of application may contribute to ensure that the transfer of the adhesive layer is correct and complete before the ring is released and removed.

In order to ensure a well-defined geometrical shape of the rolled-up portion the catheter must in its supply condition be arranged on the penis glans to avoid that the adhesive layer on the inside of the ring contacting the distal end of the catheter arranged on the penis glans, the urinary incontinence device in this embodiment also preferably comprises an applicator member placed against the rolled-up portion of the catheter in its supply condition and accommodating the distal end of same, imparting a well-defined geometry to the rolled-up portion to facilitate application and to serve as a guide during arrangement of the ring-shaped member for preventing contact between the adhesive layer placed on the inside of same and the outside of the distal end of the catheter.

BRIEF DESCRIPTION OF THE DRAWINGS

The invention is further explained in the following with reference to the schematical drawing in which.

DESCRIPTION OF THE PREFERRED EMBODIMENTS

Figure 1:
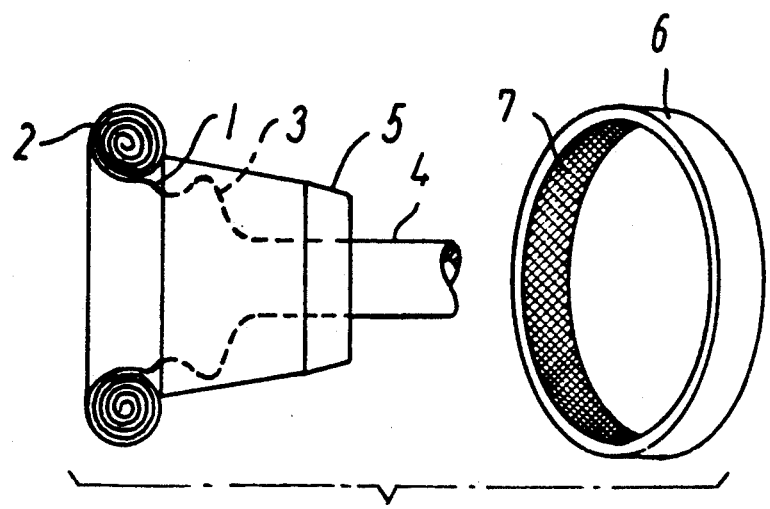
FIGS. 1, 2 and 3 show a first embodiment of the urinary incontinence device according to the invention.
Figure 2:
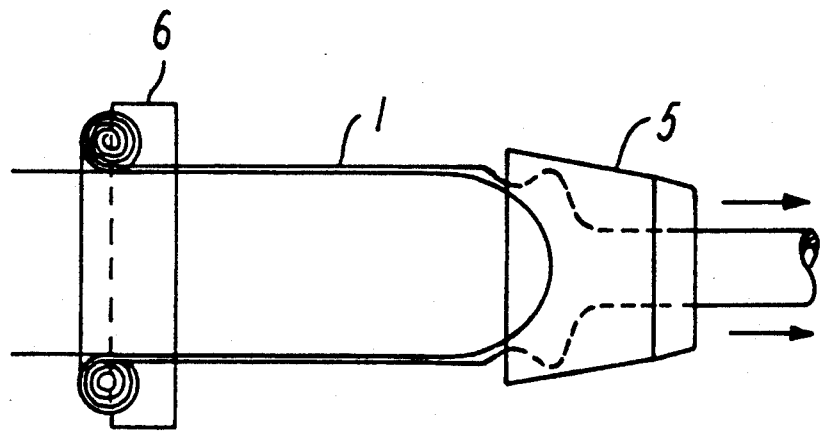
Figure 3:
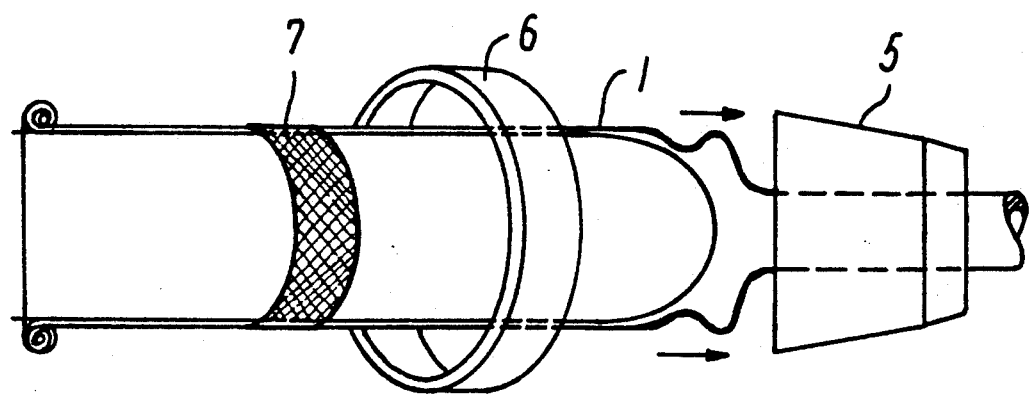

In the embodiment shown in FIGS. 1-3 the urinary incontinence device according to the invention comprises a catheter 1, which in the supply condition as shown in FIG. 1 is rolled up on part of its length from the open proximal end, whereby the rolled-up part forms a bead 2. At its distal end the catheter 1 is provided with an anti-kink chamber 3 and a narrowed drainage tube in a manner know per se, to which a not shown hose can be connected leading to a likewise not shown urine collection bag that is fastened to the user's leg.

In the supply condition the distal end of the catheter is accommodated in an open ring-shaped applicator member 5, abutting on and retaining the rolled-up bead 2, so that during application the distal end of the catheter can be placed on the penis glans by means of the applicator ring 5, whereby it is ensured that the bead 2 gets a well-defined geometrical circular shape before being applied.

In addition, the device comprises a separate annular member 6, which in the shown embodiment consists of a relatively inexpensive cardboard ring having a short axial length. The inside of the cardboard ring 6 is provided with a double-faced adhesive layer, e.g. in the form of an adhesive tape 7, underneath which the cardboard ring 6 is provided with a not shown layer of an adhesive release agent known per se such as, e.g. a silicon layer.

After the catheter 1 has been arranged on the penis glans by means of the applicator 5 the cardboard ring 6 is passed over the applicator ring 5 and touches the rolled-up bead 2, the inner diameter of the applicator ring 6 being identical to or a bit smaller than the outer diameter of the bead 2. During continued moving of the cardboard ring 6 the adhesive tape 7 will be released from the cardboard ring 6 and transferred to the outside of the bead 2 on a portion that that corresponds to the axial length of the cardboard ring, since the bead is carried along with the continued movement of the cardboard ring, whereby the catheter is rolled out. When the diameter of the bead decreases during the rolling-out process the cardboard ring 6 will be released and can be removed together with the applicator ring.

FIG. 3 shows the catheter 1 in near fully rolled-out condition with the adhesive tape 7 forming a seal between the inside of the catheter and the penis.

Figure 4:
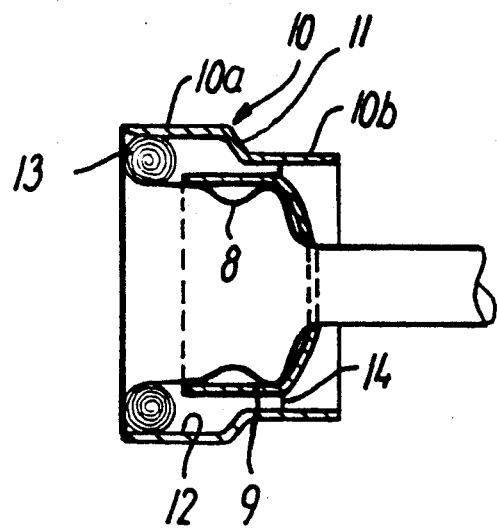
FIG. 4 a second embodiment.

In the embodiment shown in FIG. 4 the applicator ring 10 is arranged in the supply condition around the rolled-up catheter 8 and the applicator member 9 enveloping its distal end.

The applicator ring 10, which here may be of plastic, has an inner recess 11, placed between a front and a rear portion of the ring 10a and 10b, respectively, of which the diameter of the rear portion is smaller than that of the front portion.

The recess 11 serves for precise localization of the adhesive layer 12 arranged inside the applicator ring.

The adhesive layer 12 may in its supply condition in order to avoid drying up and in a manner known per se be provided with a tear-off cover foil which is removed prior to application.

In order to avoid this additional operation in connection with the application process the entire device can be supplied as a single integral unit in an embodiment as shown in FIG. 4, where the applicator ring 10 is fixed in relation to the rolled-up catheter 8, because the bead 13 formed by the rolled-up part of the catheter 8 is in contact with the proximal end of the adhesive layer 12.

As opposed to known catheters with an integrated adhesive layer there is here only a slight linear contact between the outer winding of the rolled-up bead and the adhesive, and the risk of the adhesive having a destructive effect on the catheter material is minimal.

In the shown embodiment operation can be simplified in that protection of the adhesive layer 12 in the supply condition is provided by a collar 14 which projects from the outside of the applicator member 9 and covers the interspace between the applicator member 9 and the applicator ring 10.

By designing the applicator ring 10 with a smaller diameter behind the recess 11 lying portion 10b it is ensured that the adhesive from the layer 12 is completely transferred to the inside of the catheter, as a continued straightening out of the rolled-up portion takes place after transfer of the adhesive before the applicator ring 10 is released.

Figure 5:
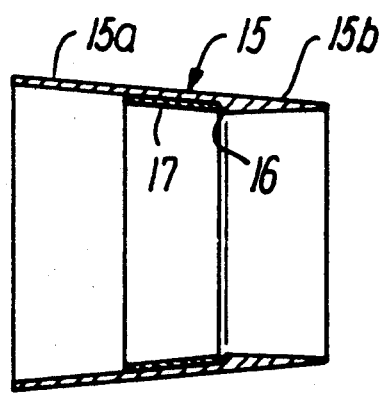
FIG. 5 a modified design of an applicator ring.

In order to obtain a good adaptation of the applicator ring to the decreasing diameter of the rolled-up bead of the catheter during rolling-out the applicator ring 15 may as shown in FIG. 5 be designed with a slightly conical inside of its front part 15a with a diameter decreasing towards the recess 16 which services for localization of the adhesive layer 17. In order to facilitate the release of the applicator ring the rear part 15b may be slightly conical in the opposite direction, i.e. with a diameter which increases from the recess 16 towards the distal end.

In the embodiment shown in FIG. 5 a suitable choice of the arrangement of the recess 16 can ensure an accurate adjustment of the arrangement of the adhesive layer transferred to the inside of the catheter.

I claim:

1. A male urinary incontinence kit, comprising an external catheter for arrangement on a penis, having a distal end with a narrowed drainage tube for connection to a hose leading to a collection bag, said catheter being folded or rolled outwardly on itself from a proximal end, so that part of its inside face is turned outward, said kit further comprising an annular member separate from the catheter with a removable adhesive layer on an inside surface of said annular member, wherein said annular member is sized to be passed over said outwardly turned portion of said inside of said catheter, so that said removable adhesive layer contacts said outwardly turned portion and is transferred thereto, providing an interior adhesive layer on said catheter for adhering said catheter to a penis.

2. The kit of claim 1, wherein said catheter is rolled up on part of its length, to form a bead, wherein said annular member is ring-shaped, made of a disposable material and has a diameter which does not exceed an outer diameter of said bead but is larger than an outer diameter of said catheter.

3. The kit of claim 2, wherein an axial length of said annular member exceeds that of said adhesive layer.

4. The kit of claim 3 wherein said annular member has a larger diameter at a proximal end thereof than in a region thereof having said removable adhesive.

5. The kit of claim 4, wherein said adhesive layer abuts an interior recess between front and rear portions of said annular member.

6. The kit of claim 1, further comprising an applicator member in contact with a rolled-up portion of said catheter and surrounding said distal end of said catheter, said applicator imparting geometry to said rolled-up portion to facilitate application and to serve as a guide during application of said annular member to prevent contact between said removable adhesive layer and an exterior surface of a distal end of said catheter.

7. The kit of claim 6, wherein said annular member surrounds said rolled-up portion and also surrounds at least a portion of said applicator that is positioned around said rolled up portion, said applicator having on its outside a collar extending between said applicator and said annular member.

8. The kit of claim 1 wherein a layer of an adhesive release agent is positioned between said annular member and said adhesive layer.

9. The kit of claim 1 wherein said adhesive layer of said annular member is covered by a tear-off foil.

10. A urinary incontinence kit comprising an external catheter for arrangement on a penis, having a distal end with a narrowed drainage tube for connection to a hose leading to a collection bag, said catheter folded or rolled outwardly on itself from a proximal end to form a bead, so that part of its inside is turned outward, said kit further comprising an annular member separate from the catheter with a removable adhesive layer on an inside surface of said annular member, wherein said annular member is sized to be passed over said outwardly turned portion of said inside of said catheter, said removable adhesive layer contacts said outwardly turned portion and is transferred thereto, providing an interior adhesive layer on said catheter for adhering said catheter to a penis wherein said annular member surrounds said rolled up catheter and is fixed in relation thereto by adherence between said bead and a proximal end edge of said adhesive layer.

11. The kit of claim 10 wherein said adhesive layer of said annular member is covered by a tear-off foil.

12. The urinary incontinence device of claim 10 wherein a layer of an adhesive release agent is positioned between said annular member and said adhesive layer.

13. A urinary incontinence kit comprising an external catheter for arrangement on a penis, said catheter having a distal end with a narrowed drainage tube for connection to a hose leading to a collection bag, said catheter being folded or rolled outwardly on itself from a proximal end so that part of its inside face is turned outward, said kit further comprising an annular member with a removable adhesive layer on an inside surface thereof, wherein said annular member is sized to be passed over said hourly outwardly turned portion of said inside of said catheter, said removable adhesive layer contacts said outwardly turned portion and is transferred thereto to provide an interior adhesive layer on said catheter for adhering said catheter to a penis, said device further comprising an applicator member in contact with a rolled up portion of said catheter and surrounding said distal end of said catheter wherein an annular collar extends outwardly from said applicator and contacts said annular member, contact being discontinued by a user moving said annular member relative to said applicator and said catheter.

* * * * *